United States Patent
Barth et al.

(10) Patent No.: US 7,380,939 B2
(45) Date of Patent: Jun. 3, 2008

(54) METHOD AND ARRANGEMENT FOR THE MEASUREMENT OF THE ANTERIOR SEGMENT OF THE EYE

(75) Inventors: Roland Barth, Jena (DE); Roland Bergner, Jena (DE); Klaus-Ditmar Voigt, Jena (DE); Frank Behrendt, Jena (DE); Burkhard Dietzel, Buergel (DE); Eberhard Hofmann, Bollberg (DE); Gert Stober, Jena (DE); Peter Klopfleisch, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 6 days.

(21) Appl. No.: 10/557,566

(22) PCT Filed: May 14, 2004

(86) PCT No.: PCT/EP2003/005170

§ 371 (c)(1),
(2), (4) Date: Nov. 21, 2005

(87) PCT Pub. No.: WO2004/103169

PCT Pub. Date: Dec. 2, 2004

(65) Prior Publication Data

US 2007/0052925 A1    Mar. 8, 2007

(30) Foreign Application Priority Data

May 22, 2003  (DE)  ............................... 103 23 920

(51) Int. Cl.
*A61B 3/10*    (2006.01)
(52) U.S. Cl. ....................................... 351/211; 351/215
(58) Field of Classification Search ......... 351/200–247
See application file for complete search history.

(56) References Cited

U.S. PATENT DOCUMENTS

| 5,474,548 | A | 12/1995 | Knopp et al. |
| 5,673,096 | A * | 9/1997 | Dorsel et al. ................ 351/211 |
| 6,409,345 | B1 * | 6/2002 | Molebny et al. ............ 351/212 |
| 2003/0038921 | A1 * | 2/2003 | Neal et al. .................. 351/212 |

FOREIGN PATENT DOCUMENTS

| DE | 44 46 183 | 6/1996 |
| DE | 198 12 050 | 9/1999 |
| DE | 198 57 001 | 6/2000 |
| DE | 101 08 797 | 9/2002 |
| DE | 101 42 001 | 3/2003 |
| DE | 101 51 314 | 4/2003 |

OTHER PUBLICATIONS

"Submicrometer Precision Biometry of the Anterior Segment of the Human Eye" (Drexler et al., Investigative Ophthalmology & Visual Science, vol. 38, No. 7, p. 1304, Jun. 1997).
"Optical Measurement of the Axial Eye Length by Laser Doppler Interferometry" (Ch. Hitzenberger, Investigative Ophthalmology and Visual Science, vol. 32, No. 3, p. 616, Mar. 1991).

* cited by examiner

*Primary Examiner*—Ricky L Mack
*Assistant Examiner*—James R Greece
(74) *Attorney, Agent, or Firm*—Reed Smith LLP

(57) ABSTRACT

The invention is directed to an arrangement and a method for measuring the anterior segment of the eye using interferometric means. The eye is illuminated by a convergent beam bundle and aligned with the optical axis of the measuring device by generating directional stimuli and accommodation stimuli by means of a display which is mirrored into the beam path.

2 Claims, 4 Drawing Sheets

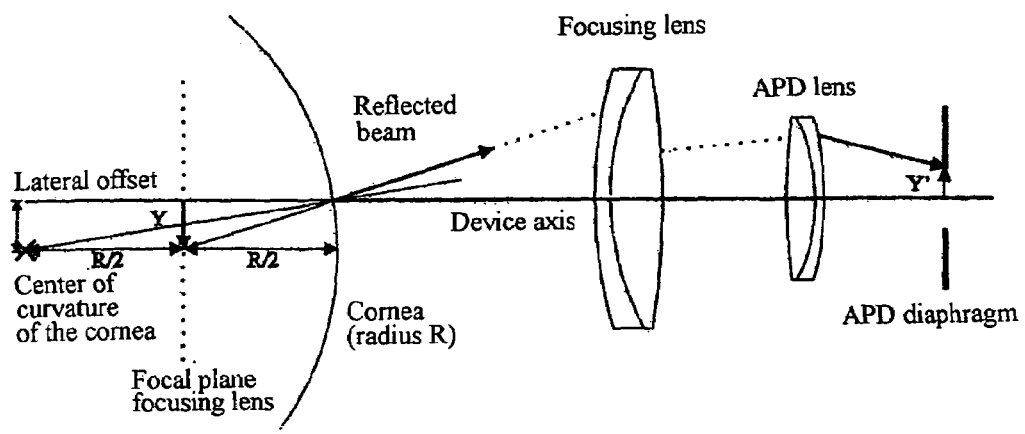
Fig. 2
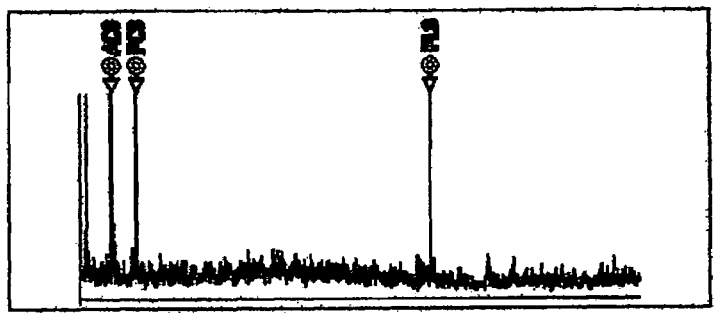
Fig. 3 (Measurement 1)
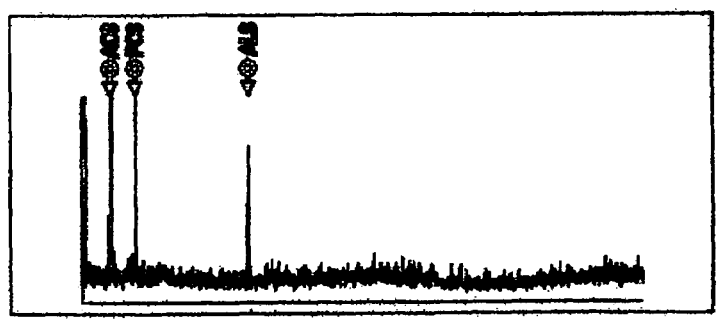
Fig. 4 (Measurement 2)

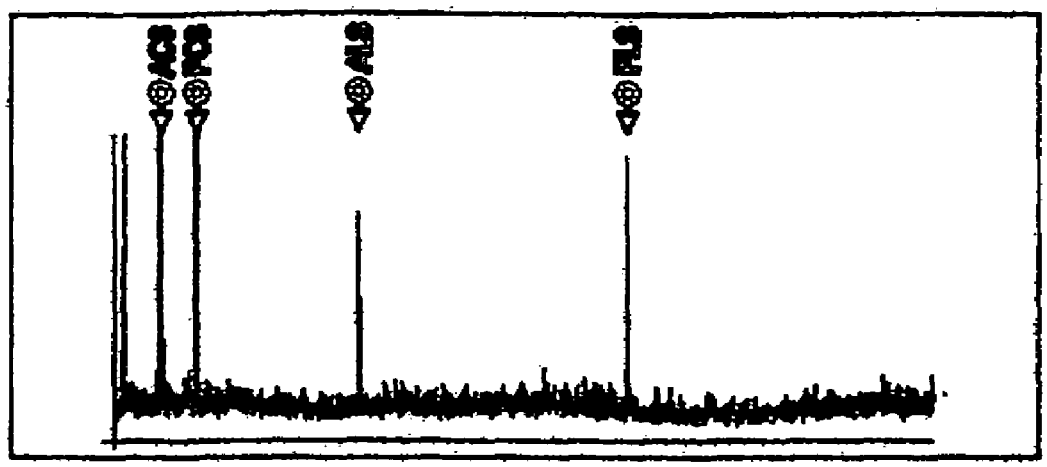
Fig. 5 (superposition)

METHOD AND ARRANGEMENT FOR THE MEASUREMENT OF THE ANTERIOR SEGMENT OF THE EYE

CROSS-REFERENCE TO RELATED APPLICATIONS

This application claims priority of International Application No. PCT/EP04/005170, filed May 14, 2004, and German Application No. 103 23 920.0, filed May 22, 2003, the complete disclosures of which are hereby incorporated by reference.

BACKGROUND OF THE INVENTION a) Field of the Invention

The invention is directed to a method and an arrangement for measuring the anterior segment of the eye. It is applicable in particular for determining the parameters needed for selecting a suitable intraocular lens for a cataract operation. Further, it can also be used for quality control subsequent to the implantation of an intraocular lens.

b) Description of the Related Art

A device that can be used for contactless measurement of the eye length, corneal curvature and anterior chamber depth is known from DE 198 57 001. In this connection, the axial length is determined interferometrically, the corneal curvature is determined by means of image processing from reflection images of measurement marks that are projected on the cornea at a determined angle, and the anterior chamber depth is determined from the evaluation of the back-scattering of a column-shaped illumination of the eye length.

The described measurement of the anterior chamber depth does not function in the presence of pseudophakia because the implanted intraocular lenses (IOL) generally do not have a scattering effect. The interferometric measurement of the axial eye length is known from "Optical Measurement of the Axial Eye Length by Laser Doppler Interferometry" (Ch. Hitzenberger, Investigative Ophthalmology and Visual Science, Vol. 32, No. 3, page 616, March 1991), which disclosure is referred to in the following.

DE 101 08 797 describes a method for determining the diameter of the pupil and iris with digital image processing means, wherein the angle between the visual axis and optical axis of the eye, among others, can also be determined.

A test setup by which the anterior segment of the eye can be measured by interferometry is described in "Submicrometer Precision Biometry of the Anterior Segment of the Human Eye" (Drexler et al., Investigative Ophthalmology & Visual Science, Vol. 38, No. 7, page 1304, June 1997). For this purpose, the eye is irradiated by a collimated light bundle during the measurement process. The light components which are reflected by the cornea and lens surfaces and are imaged on a photodetector are relatively weak. The eye must be oriented for measurement in such a way that its optical axis coincides with the measurement axis of the device. For this purpose, a collimated fixating light is presented to the patient along a stationary (coaxial) axis, which fixating light is coupled in by a mirror for the eye to be measured. The adjustment of an angle between the visual axis of the patient and the measurement axis of the test setup is carried out by means of a scanning mirror. Even with a deviation of the optical axis from the measurement axis in the range of 1° (e.g., due to fixating problems or nystagmus), the reflections of the cornea and lens can no longer overlap so that there is no interference measurement signal. Accordingly, the measurement is very sensitive to tilting of the patient's eye. Further, the fixating light always appears in infinity to the patient, which can be disadvantageous. The position of the optical axis is found by tilting the scanning mirror in two directions orthogonal to one another until all measurement signals of the cornea and lens are to be detected simultaneously. This method is extremely time-consuming and also does not lead to the desired results in all patients. This method is too complicated for routine clinical use.

OBJECT AND SUMMARY OF THE INVENTION

The primary object of the invention is to overcome the disadvantages of the prior art and to enable a fast and reliable measurement of the anterior segment of the eye by interferometric means.

This object is met, according to the invention, by an arrangement for measuring the anterior segment of the eye of a patient comprising an interferometer arrangement is provided for measuring the distances of optical functional surfaces of the eye, a light source which is provided for generating a focus stimulus for the patient and a focusing lens which is provided in the beam path of the interferometer. The focusing lens illuminates the eye with a convergent beam bundle. The light source for generating the focusing stimulus is a surface light modulator with adjustable light distribution.

BRIEF DESCRIPTION OF THE DRAWINGS

In the drawings:

The invention will be described in the following with reference to the drawings.

FIG. 2 shows a schematic view of a portion of the interferometer beam path;

FIGS. 3 and 4 show two (incomplete) measurement results;

FIG. 5 shows a complete measurement result; and

DESCRIPTION OF THE PREFERRED EMBODIMENTS

Figure 1:
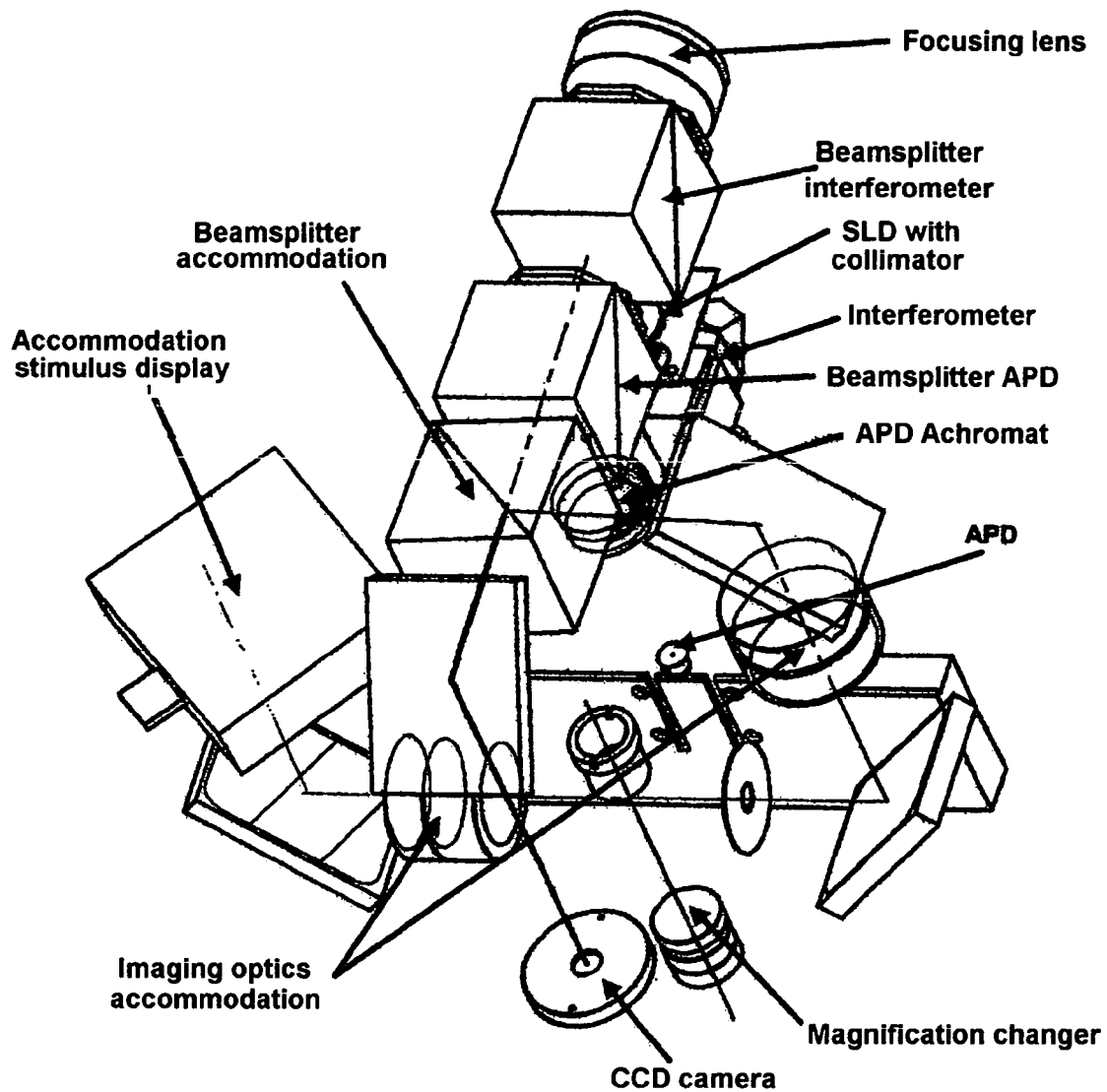
FIG. 1 shows a schematic arrangement of a preferred embodiment example.

In FIG. 1, the light emitted by an SLD (superluminescent diode) is guided in direction of the patient's eye (not shown) in a known manner by an interferometer and a beamsplitter interferometer. A focusing lens which focuses the measuring beam in the anterior segment of the eye is located between the beamsplitter and the eye. The light reflected by the eye is approximately collimated through the focusing lens and is imaged on the photodetector APD (Avalanche Photo Detector), which is located behind a diaphragm, not shown, by means of beamsplitters APD and APD Achromat. A small proportion of the light (about 5%) is transmitted in the beamsplitter and imaged on a CCD camera by suitable optics (magnification changer).

By deliberate defocusing of the measurement beam by means of the focusing lens or displacement of the optics relative to the patient's eye along the optical axis of the arrangement, the reflections of the cornea and lens (the front and back, respectively) are imaged out of focus and in magnified form upon the photodetector APD. The magnified imaging of the reflections makes it possible to overlap the reflections in a large area so as to reduce sensitivity to tilting and lateral displacement of the eye. Varying degrees of light intensities of the reflections on the APD are advantageously compensated through corresponding adaptation of the electronic amplification. The amplification can be adapted automatically or reduced by an average constant factor.

Further, the sensitivity of the arrangement to deviations of the eye axis from the optical axis of the arrangement depends upon the ratio of the focal length of the focusing lens to the focal length of the APD Achromat (APD lens). The greater the quotient of the two focal lengths, the lower this sensitivity, so that larger deviations also still deliver a signal that can be evaluated.

FIG. 2 shows this dependency of the lateral adjustment accuracy to the eye upon the focal lengths of the lenses that are used. The eye is offset laterally relative to the device axis (optical axis) by y. The main beam must pass the APD diaphragm (Ø=2y') after reflection at the cornea and passage through the focusing lens and APD lens. The APD diaphragm lies in the focal plane of the APD lens.

The imaging of the virtual object point (height y) in the focal plane of the focusing lens is taken into account in order to determine the dependency of the allowable lateral offset upon the focal lengths of the lenses. For the imaging of this imaginary object on the edge of the APD diaphragm:

$$y' \approx \frac{f_{APD}}{f_{FOK}} y$$

and, therefore, for the lateral offset $$y \approx \frac{f_{FOK}}{f_{APD}} y',$$

where $f_{FOK}$, $f_{APD}$ are the focal lengths of the focusing lens and APD lens, y is the permissible lateral offset, and y' is half of the diaphragm diameter.

An optimal value for this ratio $f_{FOK}$:$f_{APD}$ is approximately between 1.5 and 4.

In the event that not all of the signals of the cornea and lens can be detected simultaneously in spite of the enlarged measurement area, a plurality of measurements are carried out and the results of these measurements are suitably combined in a total result containing all necessary measurement signals. FIGS. 3 to 5 show a possibility for a method of this kind, wherein ACS is the anterior cornea surface, PCS is the posterior cornea surface, ALS is the anterior lens surface, and PLS is the posterior lens surface.

No reflection signal of the anterior lens surface (ALS) was detected in FIG. 3. In FIG. 4, the reflection of the posterior lens surface is absent. In a first step, the two measurement series are transformed to a reflection present in both, preferably the reflection of the anterior cornea surface (ACS). Subsequently, the other values of the reflection signals from the two measurements are taken over in the total measurement. Depending on the quality of the measurements and on requirements, more than two measurements can also be carried out and combined in the manner described above. It is advantageous when the maximum values associated with the reflections from the different measurements are taken over in the total measurement.

For carrying out measurements, it is advantageous when the optical axis of the measurement arrangement and the optical axis of the eye are aligned to one another. The piercing point of the visual axis through the pupil is marked by reflection of a coaxial LED which is arranged in the optical axis of the measurement arrangement (not shown in FIG. 1 for reasons of simplicity) on which the patient is fixated. The deviation of the visual axis from the optical axis of the eye can then be determined by means of the method described in DE 101 08 797.

An LC display (accommodation stimulus display) which is integrated in the device is used for the adjustment of the angle required for measurement and is mirrored into the beam path by an imaging optics accommodation and a beamsplitter accommodation. A test mark (e.g., cross, point, or the like) is automatically displaced as a function of this determined deviation in such a way that the patient's eye is oriented for measurement by fixating on this mark. The detectability of this LED is decisively improved by the focusing lens, which contributes to increasing the measuring accuracy.

Mirroring the test marks shown in the LC display in the visible wavelength range into the measurement beam path (infrared) makes specific demands on the beamsplitter being used (beamsplitter accommodation). For this purpose, the efficiency of the optical signal to be coupled in from the LC display into the beam path leading to the patient's eye needs to be as high as possible. The characteristic whereby, due to its operating principle, the light coming from the LC display is linearly polarized is made use of in order to meet this demand. The beamsplitter has a reflection of virtually 100 percent for s-polarized light in the VIS range from 400 nm to 650 nm. At the same time, lossless transmission, as far as possible, is realized in the near infrared range (830 nm . . . 1000 nm).

The layer design meets these requirements for an incident angle range around 45°. The materials that are used are matched with one another with respect to the refractive index of the substrate, cement and coating substances. The following materials were selected for this specific use:

| Substrate: | BK7 | n = 1.64 |
| | cement | n = 1.52 |
| | H | n = 2.30 |
| | L | n = 1.48. |

The design comprises twenty-three alternating layers of H and L.

Corresponding components can be produced for comparable splitters by a suitable selection of the refractive indices of the substrate and coating substances and the incident angle. The complete layer system can be displaced by a factor with respect to the edge position.

Parameters: high reflection of 400 nm . . . 660 nm, s-polarized
   high transmission of 830 nm . . . 1000 nm, unpolarized and s-polarized Example Data:

| 1 | TiO2 | 66.28 nm |
| 2 | SiO2 | 91.88 nm |
| 3 | TiO2 | 102.33 nm |
| 4 | SiO2 | 141.87 nm |
| 5 | TiO2 | 75.32 nm |
| 6 | SiO2 | 156.86 nm |

-continued

| | | |
|---|---|---|
| 7 | TiO2 | 75.32 nm |
| 8 | SiO2 | 156.86 nm |
| 9 | TiO2 | 75.32 nm |
| 10 | SiO2 | 156.86 nm |
| 11 | TiO2 | 77.62 nm |
| 12 | SiO2 | 130.85 nm |
| 13 | TiO2 | 63.37 nm |
| 14 | SiO2 | 133.9 nm |
| 15 | TiO2 | 49.88 nm |
| 16 | SiO2 | 113.15 nm |
| 17 | TiO2 | 49.88 nm |
| 18 | SiO2 | 113.15 nm |
| 19 | TiO2 | 49.88 nm |
| 20 | SiO2 | 113.15 nm |
| 21 | TiO2 | 64.76 nm |
| 22 | SiO2 | 118.7 nm |
| 23 | TiO2 | 41.83 nm |

Figure 6:
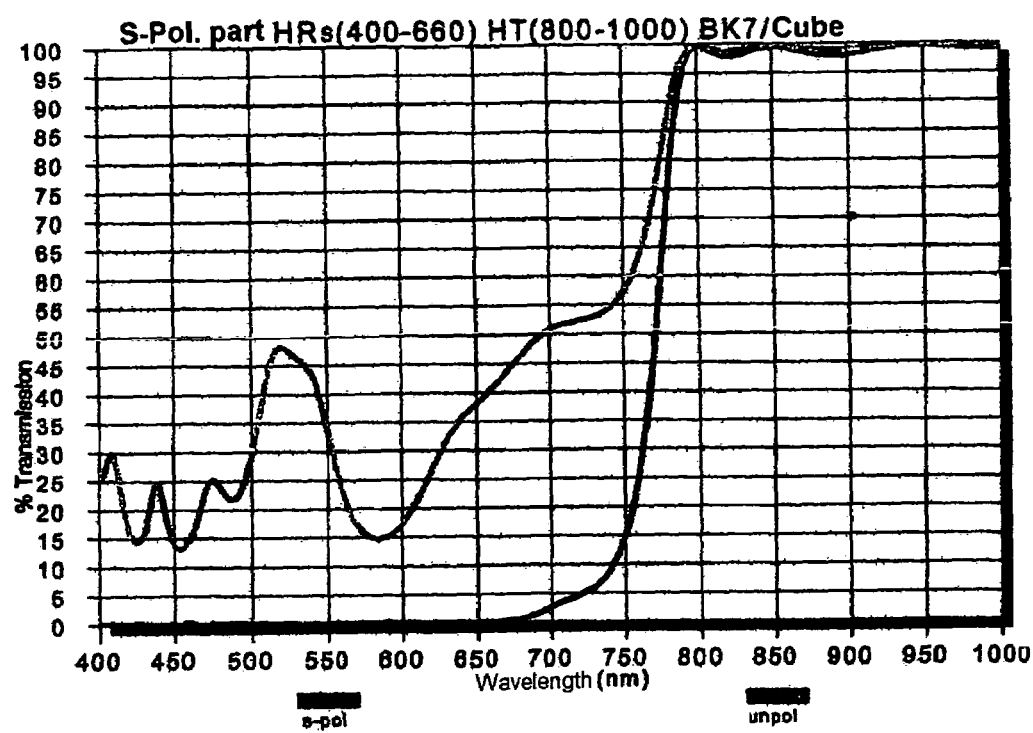
FIG. 6 shows the transmission characteristic of one of the beamsplitters from FIG. 1.

FIG. 6 shows the transmission values for s-polarized and unpolarized light which are achieved with this layer construction.

The same display is advantageously used to cause the eye to accommodate.

The imaging optics accommodation images test marks in infinity in a defined position of the display. The patient can view the displayed tests in the non-accommodated state. The imaging of test marks is carried out at defined distances in front of the patient's eye (e.g., 40 cm) by means of (e.g., motor-actuated) displacement of the display perpendicular to its extension. The patient can only see the tests sharply when he or she is accommodated. When a measurement is carried out in the anterior segment of the eye in different accommodation states that can be achieved in this way, the respective distance of the anterior lens and posterior lens from the cornea can be determined so that the movements or changes in the shape of the eye lens that are responsible for accommodation can be detected. This can also be used in particular for monitoring the efficiency of accommodating intraocular lenses.

Further, by evaluating the position of the display in which the patient can still see sharply, it is possible to determine the accommodation amplitude.

Another advantage of the solution according to the invention is the possibility of adapting the measurement arrangement to possible defective vision of the patient by corresponding displacement of the LC display until the patient sees the displayed test marks sharply.

For certain applications (e.g., prior to Lasik OP), it is important to measure the cornea thickness at a plurality of points. For this purpose, fixation stimuli (e.g., crosses, points, or the like) are displayed on the LC display at different predetermined locations. This causes the patient to change the direction of gaze in a corresponding manner so that the subsequent measurements of the cornea thickness are carried out at the predetermined point. Predetermined points of this kind can be along the eye axis but also at a distance of 1.5 mm, 3 mm, and 4.5 mm from the axis. It is also possible to realize these target points by means of correspondingly arranged discrete LEDs.

The realization of the invention is not limited to the embodiment example shown herein. Further developments are possible without departing from the scope of protection.

While the foregoing description and drawings represent the present invention, it will be obvious to those skilled in the art that various changes may be made therein without departing from the true spirit and scope of the present invention.

The invention claimed is:

1. An arrangement for measuring the anterior segment of the eye of a patient, comprising:
    an interferometer arrangement being provided for measuring the distances of optical functional surfaces of the eye;
    a light source being provided for generating a focus stimulus for the patient;
    a focusing lens being provided in the beam path of the interferometer, which focusing lens illuminates the eye with a convergent beam bundle; and
    said light source for generating the focusing stimulus being a surface light modulator with adjustable light distribution;
    wherein the ratio of the focal length of the focusing lens to the focal length of a lens associated with a detector of the interferometer arrangement is 1:1.5 to 1:4.

2. A beamsplitter for mirroring a surface light modulator into a beam path of an arrangement comprising:
    an interferometer arrangement being provided for measuring the distances of optical functional surfaces of the eye;
    a light source being provided for generating a focus stimulus for the patient;
    a focusing lens being provided in the beam path of the interferometer, which focusing lens illuminates the eye with a convergent beam bundle; and
    said light source for generating the focusing stimulus being a surface light modulator with adjustable light distribution; and
    wherein said beam splitter provides that the reflection for s-polarized light in the visible wavelength range is near 100 percent and transmission for s-polarized and unpolarized light in the infrared wavelength range is virtually 100 percent.

* * * * *